United States Patent [19]

Sasajima et al.

[11] 4,039,670
[45] Aug. 2, 1977

[54] BUTYROPHENONE COMPOUNDS AS PSYCHOTROPICS

[75] Inventors: Kikuo Sasajima, Toyonaka; Keiichi Ono, Nishinomiya; Masaru Nakao, Toyonaka; Hisao Yamamoto, Higashinada, all of Japan

[73] Assignee: Sumitomo Chemical Co., Ltd., Osaka, Japan

[21] Appl. No.: 568,819

[22] Filed: Apr. 17, 1975

[30] Foreign Application Priority Data

Apr. 18, 1974 Japan .................. 49-44181

[51] Int. Cl.² .................. C07D 487/10; A01N 9/22
[52] U.S. Cl. .................. 424/267; 260/251 R; 260/293.6; 260/293.66; 260/293.8; 260/295 M; 260/297 R; 424/248.57; 424/250; 424/263; 544/175
[58] Field of Search .................. 260/293.66; 424/267

[56] References Cited

U.S. PATENT DOCUMENTS 3,238,216  3/1966  Janssen .................. 260/293.4

Primary Examiner—Cecilia M. S. Jaisle
Attorney, Agent, or Firm—Birch, Stewart, Kolasch and Birch

[57] ABSTRACT

Butyrophenone compounds having excellent psychotropic activities represented by the formula:

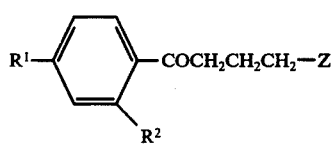

wherein $R^1$ is a halogen atom, $R^2$ is a lower alkyl group, and Z is a group of either one of the formulae:

(1)

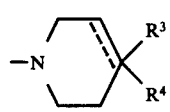

(wherein the dotted line indicates the optional presence of an additional single bond linkage, $R^3$ is a hydrogen atom or a hydroxyl group but only when said additional single bond linkage is not present and $R^4$ is a hydrogen atom or a phenyl or benzyl group optionally substituted with one or two substituents selected from the group consisting of halogen, lower alkyl, lower alkyoxy and trifluoromethyl on the benzene ring (except monohalophenyl)), (2)

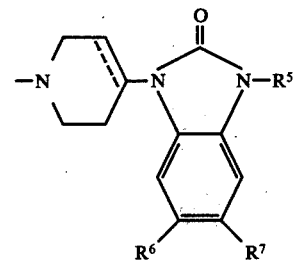

(wherein the dotted line indicates the optional presence of an additional single bond linkage, $R^5$ is a hydrogen atom or a lower alkyl group and $R^6$ and $R^7$ are each a hydrogen atom, a halogen atom or a lower alkyl group), (3)

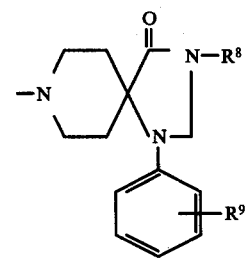

(wherein $R^8$ is a hydrogen atom or a lower alkyl group and $R^9$ is a hydrogen atom, a halogen atom, a lower alkyl group or a lower alkoxy group), (4)

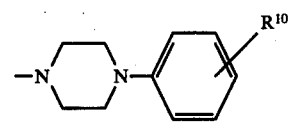

(wherein $R^{10}$ is a hydrogen atom, a halogen atom, a lower alkyl group, a lower alkoxy group or a trifluoromethyl group), or (5)

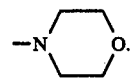

7 Claims, No Drawings

BUTYROPHENONE COMPOUNDS AS PSYCHOTROPICS

The present invention relates to novel butyrophenone compounds, to pharmaceutical compositions containing them, and to processes for the production thereof.

The said novel butyrophenone compounds are representable by the formula:

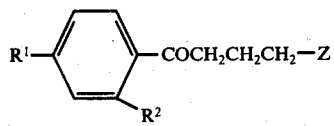

[I]

wherein $R^1$ is a halogen atom, $R^2$ is a lower alkyl group and Z is a group of either one of the formulae:

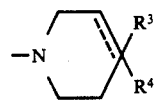

(wherein the dotted line indicates the optional presence of an additional single bond linkage, $R^3$ is a hydrogen atom or a hydroxyl group but is not present in case of the dotted line indicating the presence of an additional single bond linkage being present and $R^4$ is a hydrogen atom or a phenyl or benzyl group optionally substituted with one or two substituents selected from the group consisting of halogen, lower alkyl, lower alkoxy and trifluoromethyl on the benzene ring (except monohalophenyl)),

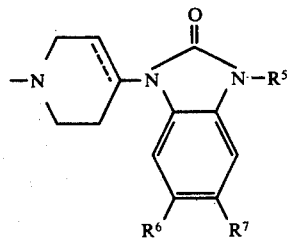

(wherein the dotted line indicates the optional presence of an additional single bond linkage, $R^5$ is a hydrogen atom or a lower alkyl group and $R^6$ and $R^7$ are each a hydrogen atom, a halogen atom or a lower alkyl group),

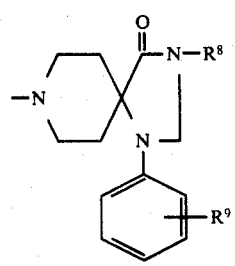

(wherein $R^8$ is a hydrogen atom or a lower alkyl group and $R^9$ is a hydrogen atom, a halogen atom, a lower alkyl group or a lower alkoxy group),

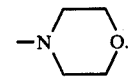

(wherein $R^{10}$ is a hydrogen atom, a halogen atom, a lower alkyl group, a lower alkoxy group or a trifluoromethyl group), and $$-N\diagdown O.$$

In the significances as defined above, "lower alkyl" and "lower alkoxy" include groups having one to about four carbon atoms and may be of straight or branched chain structure. Examples thereof are methyl, ethyl, n-propyl, isopropyl, n-butyl, isobutyl, t-butyl, methoxy, ethoxy, n-propoxy, isopropoxy, n-butoxy, isobutoxy and t-butoxy. The term "halogen" includes fluorine, chlorine, bromine and iodine.

With respect to he symbol $R^4$, it may be monosubstituted phenyl such as lower alkylphenyl, lower alkoxyphenyl or trifluoromethylphenyl, monosubstituted benzyl such as halobenzyl, lower alkylbenzyl, lower alkoxybenzyl or trifluoromethylbenzyl, disubstituted phenyl such as dihalophenyl, lower alkyl-halophenyl, lower alkoxy-halophenyl, halo-trifluoromethylphenyl, lower alkyl-lower alkoxyphenyl, lower alkyl-trifluromethylphenyl, lower alkoxy-trifluoromethylphenyl, di(lower)alkylphenyl, di(lower)alkoxyphenyl or ditrifluloromethylphenyl, or disubstituted benzyl such as dihalobenzyl, lower alkyl-halobenzyl, lower alkoxy-halo-benzyl, halo-trifluoromethylbenzyl, lower alkyl-lower alkoxybenzyl, lower alkyl-trifluoromethylbenzyl, lower alkoxy-trifluoromethylbenzyl, di(lower)alkylbenzyl, di(lower)alkoxybenzyl or ditrifluoromethylbenzyl.

The preferred compounds are, with respect to formula [I], those in which $R^1$ is fluorine and $R^2$ is methyl.

The butyrophenone compounds [I] in the free base or salt form show various pharmacological activities, and their excellent central nervous system depressing activity is particularly notable. Thus, they are useful as medicines such as neuroleptics and analgesics.

In British Pat. No. 1,141,664, there are described the butyrophenone compounds of the general formula:

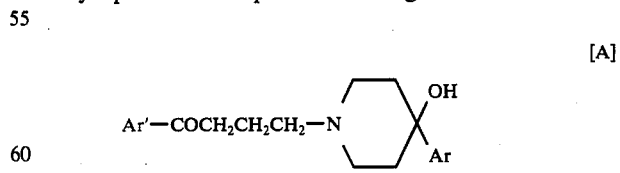

[A]

(wherein Ar is halphenyl and Ar' is dihalophenyl or lower alkyl-halophenyl), which are useful as central nervous system depressants. In this patent, the compound of the formula:

[B]

-continued

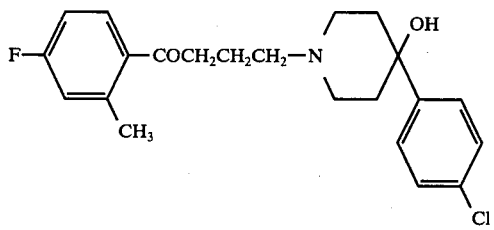

is the only compound as specifically disclosed.

It has now unexpectedly been found that the butyrophenone compounds [I], i.e. those of the formula [A] but having a group of the formula: —Z (wherein Z is as defined above) instead of the 4-halophenyl-4-hydroxyl-substituted piperidino group, have a more excellent central nervous system depressing activity than that of the compounds [A] themselves. For instance, the anti-apomorphine activity of the butyrophenone compounds [I] in rats is greater than that of the compound [B].

Accordingly, an object of the present invention is to provide novel butyrophenone compounds [I] havng a central nervous sytem depressing acitivity, Another object of this invention is to provide a process for producing the butyrophenone compounds [I]. These and other objects will be apparent to those skilled in the art to which the present invention pertains from the foregoing and subsequent descriptions.

According to the present invention, the butyrophenone compounds [I] can be prepared by reacting a compound of the formula:

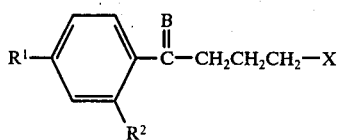

[II]

wherein $R^1$ and $R^2$ are each as defined above, X is a reactive ester residue derivable from an alcoholic group such as halogen (e.g. chlorine, bromine), arylsulfonyloxy (e.g. benzenesulfonyloxy, toluenesulfonyloxy) or alkylsulfonyloxy (e.g. methanesulfonyloxy) and B is a free or protected keto group (e.g. keto, ethylenedioxy, ethylenedithio) with a compound of the formula:

H—Z   [III]

wherein Z is as defined above to give a compound of the formula:

[IV]

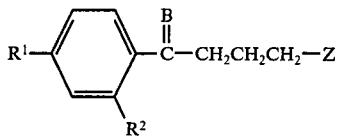

wherein $R^1$, $R^2B$ and Z are each as defined above, optionally followed by hydrolysis of the later.

The condensation reaction of the compound [II] with the compound [III] in the free base or salt form is usually carried out in an inert solvent such as an aromatic hydrocarbon (e.g. benzene, toluene, xylene), an amide (e.g. dimethylformamide, dimethylacetamide), an ether (e.g. dioxane, tetrahydrofuran), an alcohol (e.g. ethanol, n-propanol, butanol, amyl alcohol), an alkanone (e.g. acetone, butanone, methylisobutylketone) or dimethylsulfoxide at a temperature within the range of room temperature to the boiling point of the solvent. Preferably, there may be used a basic substance such as an alkali carbonate (e.g. sodium carbonate, potassium carbonate), an alkali hydrogen carbonate (e.g. sodium hydrogen carbonate, potassium hydrogen carbonate), an alkali hydroxide (e.g. sodium hydroxide, potassium hydroxide) or an organic amine (e.g. pyridine, triethylamine) as an acid binding agent. There may be also used a small amount of a reaction accelerating agent such as potassium iodide.

The hydrolysis can be carried out by a conventional acid hydrolyzing procedure. For instance, it can be accomplished by treating the compound [IV]with an acidic substance such as a mineral acid (e.g. hydrochloric acid, sulfuric acid, phosphoric acid), an organic acid (e.g. oxalic acid, tartaric acid) or an acidic ion exchange resin in water or an alkanol (e.g. methanol, ethanol, propanol), usually under a mild condition, e.g. at roomm temperature. Further, it may be accelerated by elevation of the temperature.

Specific examples of the butyrophenone compound [I] are as follows:

1-[γ-(2-Methyl-4-fluorobenzoyl)propyl]-4-(3-trifluoromethylphenyl)-4-hydroxypiperidine;
8-[γ-(2-Methyl-4-fluorobenzoyl)propyl]-4-oxo-1-phenyl-1,3,8-triazaspiro[4,5]decane;
1-[γ-(2-Methyl-4-fluorobenzoyl)propyl]-4-(2-keto-1-benzimidazolinyl)piperidine;
1-[γ-(2-Methyl-4-fluorobenzoyl)propyl]-4-(2-keto-1-benzimidazolinyl)-1,2,3,6--tetrahydropyridine;
1-[γ-(2-methyl-4-fluorobenzoyl)propyl]-4-(2-methoxyphenyl)piperazine;
1-[γ-(2-Methyl-4-fluorobenzoyl)propyl]-4-benzyl-4-hydroxypiperidine;
1-[γ-(2-Methyl-4-fluorobenzoyl)propyl]-4-(4-chlorobenzyl)-4-hydroxypiperidine;
N-[γ-(2-Methyl-4-fluorobenzoyl)propyl]-morpholine;
1-[γ-(2-Methyl-4-chlorobenzoyl)propyl]-4-(3-triflsuromethylphenyl)-4-hydroxypiperidine;
8-[γ-(2-Methyl-4-chlorobenzoyl)propyl]-4-oxo-1-phenyl-1,3,8-triazaspiro[4,5decane;
1-[γ-(2-Methyl-4-fluorobenzoyl)propyl]-4-(3-trifluoromethyl-4-chlorophenyl)-4-hydroxypiperidine;
1-[γ-(2-Methyl-4-fluorobenzoyl)propyl]-4-(3,4-dichlorophenyl)-4-hydroxypiperidine;
1-[γ-(2-Methyl-4-fluorobenzoyl)propyl]-4-(3-chloro-4-methylphenyl)-4-hydroxypiperidine, etc.

These butyrophenone compounds [I] in the free base form can be converted into their pharmaceutically acceptable salts such as acid addition salts or quaternary ammonium salts by treatment with mineral acids (e.g. hydrochloric acid, hydrobromic acid, sulfuric acid, phosphoric acid), organic acids (e.g. acetic acid, citric acid, oxalic acid, lactic acid, succinic acid, tartaric acid, cinnamic acid, ascorbic acid), alkyl halides, aralykyl halides, aromatic sulfonates or the like.

The pharmacological evaluation in animal tests has demonstrated that the butyrophenone compounds [I] show a variety of depressing activities on the central nervous system and are useful as medicines such as neuroleptics or analgesics. For instance, they exhibit an anti-apomorhine activity in rats greater than that of Chlorpromazine or the above mentioned compound [B].

Each of the butyrophenone compounds [I] may be brought into a form suitable for administration according to a method known per se.

For the preparation of pharmaceutical compositions, they may be mixed with carriers or diluents such as water, sesame oil, calcium phosphate, starch, talcum, casein, magnesium stearate, methyl cellulose, polyglycols, tragacanth and the like, sometimes together with stabilizers and/or emulsifying agents.

The resulting mixture may be processed in accordance with conventional procedures to tablets, capsules, pills, ampoules and the like. The usual oral dosage is 1-200 mg per os daily.

Practical and presently preferred embodiments of the present invention are illustratively shown in the following Examples, which are not intended to limit the scope of the invention thereto.

EXAMPLE 1

A mixture of 3 g of 4-chloro-1-(2-methyl-4-fluorophenyl)-1,1-ethylenedioxybutane, 2.3 g. of 4-oxo-1-phenyl-1,3,8-triazaspiro[4,5]decane, 1.4 g of anhydrous potassium carbonate, 0.05 g of potassium iodide and 30 ml of dimethylformamide was refluxed for 3 hour. The resulting mixture was poured into ice water. The precipitated crystals were collected by filtration and washed with water to give 8-[4-(2-methyl-4-fluorophenyl)-4,4-ethylenedioxybutyl]-4-oxo-1-phenyl-1,3,8-triazaspiro[4,5]decane as crude crystals (5 g).

A mixture of 5 g of the crude crystals, 70 ml of methanol, 21 ml of water and 11 ml of concentrated hydrochloric acid was refluxed for 50 minutes. The resulting mixture was concentrated in vacuo. The residual oil was diluted with water, made alkaline with 28% aqueous ammonia and extracted with chloroform. The extract was washed with water, dried over anhydrous sodium sulfate and concentrated in vacuo to give 8-[γ-(2-methyl-4-fluorobenzoyl)propyl]-4-oxo-1-phenyl-1,3,8-triazaspiro[4,5]decane, melting at about 179.5°-181.5° C.

EXAMPLE 2

A mixture of 3 g of 4-chloro-1-(2-methyl-4-fluorophenyl)-1,1-ethylenedioxybutane, 2.5 g of 4-(3-trifluoromethylphenyl)-4-hydroxypiperidine, 1,4 g of anhydrous potassium carbonate, 0.05 g of potassium iodide and 30 ml of dimethylformamide was refluxed for 3 hours. The resulting mixture was poured into ice water and was extracted with ethyl acetate. The extract was washed with water, dried over anhydrous sodium sulfate and concentrated in vacuo. To the residual oil were added 60 ml of methanol, 21 ml of water and 10.5 ml of concentrated hydrochloric acid. The mixture was refluxed for 50 minutes and concentrated in vacuo. The residual oil was made alkaline with 28 % aqueous ammonia and extracted with ethyl acetate. The extract was washed with water, dried over anhydrous sodium sulfate and concentrated. The residual solid was recrystallized from isopropyl ether to give 1-[γ-(2-methyl-4-flourobenzoyl)-propyl]-4-(3-trifluoromethylphenyl)-4-hydroxypiperidine, melting at about 63.5°-64.5+ C.

What is claimed is:

1. A compound of the formula:

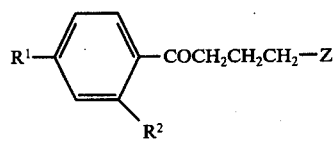

wherein $R^1$ is a halogen atom, $R^2$ is a lower alkyl group and Z is a group of the formula:

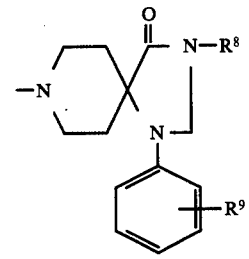

wherein $R^8$ is a hydrogen atom or a lower alkyl group and $R^9$ is a hydrogen atom, a halogen atom, a lower alkyl group or a lower alkoxy group, or a pharmaceutically acceptable acid addition salt thereof.

2. 8-[γ-(2-Lower alkyl-4-halobenzoyl)propyl]-4-oxo-1-phenyl-1,3,8-triazaspiro[4,5]decane, or a pharmaceutically acceptable acid addition salt thereof.

3. 8-[γ-(2-Methyl-4-fluorobenzoyl)propyl]-4-oxo-1-phenyl-1,3,8-triazaspiro[4,5]decane, or a pharmaceutically acceptable acid addition salt thereof.

4. The compound according to claim 1, wherein $R^1$ is fluorine.

5. The compound according to claim 1, wherein $R^2$ is methyl.

6. The compound according to claim 1, wherein $R^1$ is fluorine and $R^2$ is methyl.

7. A neuroleptic and analgesic composition comprising an effective neuroleptic and analgesic amount of the compound of claim 1 or a pharmaceutically acceptable acid addition salt thereof, and at least one pharmaceutically acceptable diluent or carrier.

* * * * *